(12) United States Patent
Jean et al.

(10) Patent No.: US 9,897,582 B2
(45) Date of Patent: Feb. 20, 2018

(54) METHOD AND SYSTEM FOR FAILURE PREDICTION USING LUBRICATING FLUID ANALYSIS

(71) Applicants: Maurice Jean, Boucherville (CA); Daniel Meilleur, Boucherville (CA)

(72) Inventors: Maurice Jean, Boucherville (CA); Daniel Meilleur, Boucherville (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 772 days.

(21) Appl. No.: 13/661,181

(22) Filed: Oct. 26, 2012

(65) Prior Publication Data

US 2014/0121994 A1    May 1, 2014

(51) Int. Cl.
  *G01N 31/22*  (2006.01)
  *G06F 15/00*  (2006.01)
  *G01N 33/28*  (2006.01)
  *F02D 41/22*  (2006.01)
  *F01M 11/10*  (2006.01)

(52) U.S. Cl.
  CPC ............ *G01N 31/22* (2013.01); *F02D 41/22* (2013.01); *G01N 33/2858* (2013.01); *G06F 15/00* (2013.01); *F01M 2011/14* (2013.01); *Y02T 10/40* (2013.01)

(58) Field of Classification Search
  CPC ........... G01N 33/2888; G01N 33/2858; G01N 15/0205; G01N 15/10; G01N 31/22; G06F 19/704; G06F 17/10; G06F 15/00
  See application file for complete search history.

(56) References Cited

U.S. PATENT DOCUMENTS

| 3,751,661 A | 8/1973 | Packer et al. |
| 3,981,584 A * | 9/1976 | Guymer ............... F01M 11/10 356/70 |
| 5,517,427 A | 5/1996 | Joyce |

(Continued)

FOREIGN PATENT DOCUMENTS

| EP | 0672243 B1 | 3/2000 |
| JP | 10330779 A | 12/1998 |

(Continued)

OTHER PUBLICATIONS

Nicolas W Farrant, Effective condition monitoring of aero-engine systems using autometed SEM/EDX and new diagnostic routines, 06241998,Rolls-Royce plc, 1-14.*

(Continued)

*Primary Examiner* — John Breene
*Assistant Examiner* — Mohammad Islam
(74) *Attorney, Agent, or Firm* — Norton Rose Fulbright Canada LLP

(57) ABSTRACT

Methods and systems for failure prediction using analysis of oil or other lubricant. Raw data about feature(s) of each of a plurality of particles filtered from a fluid sample are used to categorize each particle into one of a plurality of categories, each category being defined by one or more of: chemical composition, size and morphology. Particle physical characteristics in each category are quantified to obtain a set of categorized data. The categorized data are compared with historical data. Results of the comparing are evaluated to generate a prediction of any failure or mechanism of failure.

19 Claims, 2 Drawing Sheets

(56) References Cited

U.S. PATENT DOCUMENTS

| | | | |
|---|---|---|---|
| 5,537,336 | A | 7/1996 | Joyce |
| 5,586,161 | A | 12/1996 | Russell et al. |
| 5,817,928 | A * | 10/1998 | Garvey, III ........ G01N 33/2888 324/698 |
| 5,982,847 | A | 11/1999 | Nelson |
| 6,435,013 | B1 | 8/2002 | Rodriguez et al. |
| 6,643,570 | B2 | 11/2003 | Bangert et al. |
| 6,859,517 | B2 | 2/2005 | Wilson et al. |
| 7,184,515 | B2 | 2/2007 | Wilson |
| 7,523,615 | B2 | 4/2009 | Singh et al. |
| 7,634,913 | B2 | 12/2009 | Singh et al. |
| 7,745,382 | B2 | 6/2010 | Sloan |
| 8,676,436 | B2 | 3/2014 | Raimarckers et al. |
| 8,805,624 | B2 | 8/2014 | Uluyol |
| 2009/0240640 | A1* | 9/2009 | Blain ................. G01N 33/2888 706/12 |
| 2010/0036619 | A1* | 2/2010 | Bolt .................. G01N 33/2888 702/50 |
| 2010/0138132 | A1 | 6/2010 | Apps et al. |
| 2011/0095190 | A1 | 4/2011 | Kommareddy et al. |
| 2011/0125475 | A1* | 5/2011 | Lugt ..................... G01M 13/04 703/7 |
| 2012/0118051 | A1* | 5/2012 | Raadnui .................. G01N 3/56 73/61.71 |
| 2012/0150491 | A1* | 6/2012 | Shi ..................... G05B 23/0235 702/184 |
| 2013/0197738 | A1* | 8/2013 | Dvorak ............. G01N 33/2858 701/29.5 |
| 2013/0197830 | A1* | 8/2013 | Dvorak ................. G06Q 10/20 702/46 |

FOREIGN PATENT DOCUMENTS

| | | | |
|---|---|---|---|
| WO | | 2008013597 A2 | 1/2008 |
| WO | WO | 2015025160 A1 | 2/2015 |

OTHER PUBLICATIONS

Amsoil, Technical service bulletin, Jul. 2, 2007, Amsoil, AF-2007-07-25,1-2.*
STIC, Search Notes, STIC, 06192014,1-24.*
Noria Corporation. http://www.machinerylubrication.com/Read/698/electron-microscopy-sem-oil "Using Electron Microscopy in Oil Analysis Applications—Comparing SEM to TEM".
Golden, "The Determination of Iron in Used Lubricating Oil," Appl. Spectrosc. 25, 668-671 (1971).
Herguth et al. "Applications of Scanning Electron. Microscopy and Energy Dispersive. Spectroscopy (SEM/EDS). To Practical Tribology Problems", Herguth Laboratories. http://www.herguth.com/technical/sem.pdf.
Vähäoja. "Oil analysis in machine diagnostics". Acta Univ. Oul. A 458, 2006.
Whitlock. "X-ray Methods for Monitoring Machinery Condition" vol. 40, 1996.
M. Lukas, D.P. Anderson. Spectro Incorporated, Littleton, Massachusetts "Rotrode Filter Spectroscopy, Does It have a Place in Commercial or Military Oil Analysis Laboratory".
K.J. Eisentraut, R.W. Newman, C.S. Saba, R.E. Kauffman, and W.E. Rhine. "Spectrometrix oil analysis: detecting engine failures before they occur", Analytical Chemistry 56, Aug. 84, 1086A-1094A.
European Patent Office; Extended European Search Report dated Jan. 3, 2017 re: European Patent Application No. 16191213.4.
Levi et al., Failure Analysis and Condition Monitoring of an Open-Loop Oil System Using Ferrography, Tribology Letters, May 12, 2009, pp. 17-29, vol. 36, No. 1, Kluwer Academic Publishers=Plenum Publishers, NE.
Canadian Intellectual Property Office, Examiner's Requisition dated Jul. 17, 2017 re: Canadian patent application No. 2,927,683.

* cited by examiner

METHOD AND SYSTEM FOR FAILURE PREDICTION USING LUBRICATING FLUID ANALYSIS

TECHNICAL FIELD

The disclosure relates generally to methods and systems for failure prediction using fluid analysis, and more particularly to methods and systems for failure prediction in engines using oil (or other lubricant) analysis.

BACKGROUND OF THE ART

The analysis of engine oil or other lubricant for the purpose of identifying premature component wearing has been performed for several decades using optical atomic spectroscopy (e.g., atomic emission spectroscopy (AES), as well as its predecessor that has been in use as a field monitoring method, atomic absorption spectroscopy (AAS)). This technology has been the basis for the military aviation's Spectroscopic Oil Analysis Program (SOAP). However, this technology may have disadvantages, such as a lack of repeatability among different equipment and an inability to analyze particles greater than 5 μm in diameter. Furthermore, SOAP typically uses optical atomic spectroscopy, which is an elemental analysis of the total oil sample and typically does not characterize individual particles in the sample.

Rotrode Filter Spectroscopy has been introduced in 1980 and it was commercialized by Spectro Incorporated (Littleton, Mass.). The method focuses mainly on the analysis of large particles in the oil and has proven to be effective to establish the source of wear material in a system already generating wear material [1].

Scanning electron microscope (SEM) equipped to perform X-ray spectroscopy has been used to characterize individual particles [2] for wear mode indicators. However, SEM has been considered to be unsuitable for routine monitoring of machine condition, for example as reported in Whitlock [3].

SUMMARY

The disclosure describes methods and systems for failure prediction using analysis of a fluid, such as oil or other lubricant. In various aspects, for example, the disclosure describes methods and systems for failure prediction using analysis of oil samples, such as from gas turbine engines.

In some example aspects, the present disclosure provides a method for failure prediction in an engine, the method being implemented by a processor, the method may include: receiving raw data representing a plurality of features of each of a plurality of particles filtered from a fluid sample obtained from the engine, the engine belonging to an engine type; wherein the plurality of features includes at least one physical characteristic and chemical composition; categorizing each particle into one of a plurality of categories according to at least one of the plurality of features by calculating a likelihood that a given particle belongs to a given category, each category being defined by one or more of: chemical composition, size and morphology; quantifying particle physical characteristics in each category to obtain a set of categorized data; comparing the set of categorized data with at least one set of historical data associated with the engine type, the historical data being retrieved from a database; evaluating results of the comparing using a set of predefined rules to generate a prediction of any failure or mechanism of failure; and generating an output indicating the prediction.

In some example aspects, the present disclosure provides a system for fluid analysis, the system may include a processor and a memory containing machine-readable instructions for execution by the processor, the machine-readable instructions causing the processor to carry out the method described above.

In some example aspects, the present disclosure provides a non-transitory computer-readable medium or media embodying computer-executable instructions configured for causing one or more processors to carry out the method described above.

Further details of these and other aspects of the subject matter of this application will be apparent from the detailed description and drawings included below.

DESCRIPTION OF THE DRAWINGS

Reference is now made to the accompanying drawings, in which.

DETAILED DESCRIPTION

Figure 1:
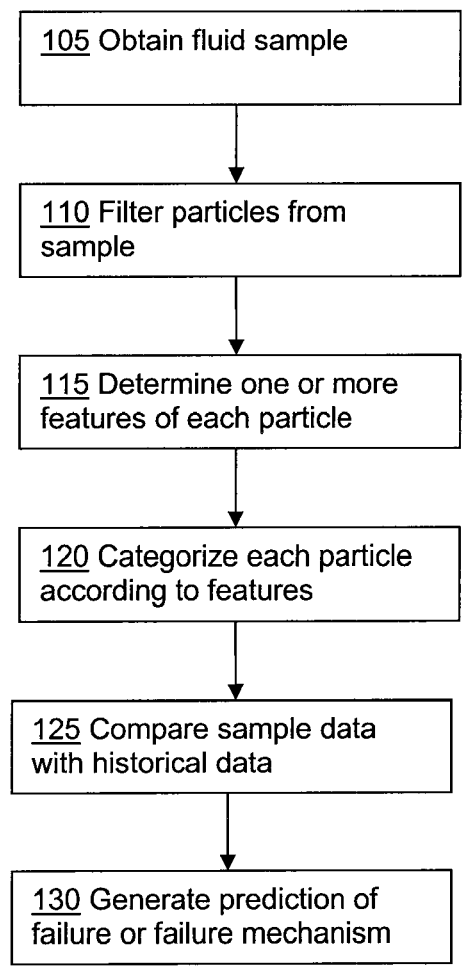
FIG. 1 is a flowchart illustrating an example of the disclosed methods for failure prediction using oil analysis.

Recently developed engines, such as gas turbine engines, may produce debris (e.g., metallic debris) in oil samples at a level of concentration below the operating zone of conventional oil analysis techniques (e.g., SOAP, which typically requires debris to be present on the order of parts per million (ppm)). It would be useful to provide methods and systems for analysis of oil (or other lubricant or fluid) samples from such engines, for example for detection of debris at the part per billion (ppb) level.

Oil analysis to perform predictive maintenance (e.g., on engines) has been performed for more than fifty years but has not been very useful to detect abnormal behavior early in the process. For example, using conventional techniques, failure is typically detected only several hours before the problem occurs, resulting in the need for the engine operator to submit oil sample at low time intervals (e.g., every 10 to 50 hours) to have a chance to capture the indication of failure before the actual failure occurs. Such a high frequency of sampling may not be practical or economical for an aircraft operator.

Considering the direct and indirect costs of any engine failure and unplanned engine removal, there is a need for methods and systems that may be able to predict failure sufficiently in advance, in order for the appropriate tasks, such as maintenance and/or decommissioning, to be scheduled and carried out.

The conventional approach for monitoring engine material wear is to perform an analysis on particles that were extracted from the engine filter. Collected debris is then typically analyzed by SEM. This method is typically costly because the engine filter is typically not reused. Further, such a method may not be practical considering that removing the engine filter may be time consuming. For such reasons, among others, filter analysis typically is not performed frequently and is mainly used to monitor engines already identified as potentially behaving abnormally. Filter analysis typically is not suitable for routine monitoring of engines.

In various aspects and examples, the disclosed methods and systems may allow for analysis of engine oil (or other lubricant) samples in order to detect abnormal behavior, based on material wear, without having to remove the engine filter. The disclosed methods and systems may be referred to as "Complete Oil Analysis Technology" (COAT).

The disclosed methods and systems may be based on the analysis of relatively small particles in oil that typically are not captured by a conventional 30 μm porosity filter. By extending the oil analysis to include smaller particles, the disclosed methods and systems may provide better understanding of engine behavior, using a relatively small oil sample. For example, it has been estimated that there are, on average, about one thousand particles sized between 0.5 μm to 30 μm per typical sample, which can be analyzed to predict engine behavior, and which typically are not considered in conventional filter analysis.

The disclosed methods and systems may thus provide a diagnostic and analytical tool based on analysis of particles in fluids, such as engine oil or other lubricant, and may provide advance detection of premature wear on specific engine parts and/or detection of failure mechanisms. The disclosed methods and systems may be suitable for failure prediction for gas turbine engines operating in the field. The disclosed methods and systems may be used for prediction of other wear events, including prediction of events other than failure, using analysis of other fluid samples, for example any suitable lubricating fluid. For example, the disclosed methods and systems may be used to identify any contaminants that have been introduced into a lubricating system (e.g., by usage in abnormal conditions or by a problem during maintenance). The disclosed methods and systems may also be used to detect any abnormal behavior of an engine component in contact with a lubrication fluid system, for example.

FIG. 1 is a flowchart illustrating an example of the disclosed methods for failure prediction using analysis of a fluid, such as engine oil or other lubricant. The example method may be carried out by any suitable processor, such as in a SEM workstation. The workstation may include one or more input devices (e.g., keyboard and mouse) for receiving user input, as well as one or more data ports and/or communication ports for receiving external data (e.g., wirelessly or through wired connections) from other processors and systems. The workstation may also include one or more output devices (e.g., one or more screens and/or printers) for displaying and/or providing a report of predicted failure mechanisms. In some examples, some or all of the method may be automated.

At 105 a fluid sample (e.g., an oil or other lubricant sample from an aircraft engine) is obtained. In the example of an oil sample from an aircraft engine, the oil sample may be collected by the aircraft operator. In some examples, more than one sample may be obtained from the engine. A relatively small amount of oil (e.g., 25 mL or less) may be sufficient. The amount of oil sample obtained may be selected in order to obtain a certain number of particles. For example, it may be known or expected that a given engine should have a certain density of particles in the oil after a certain number of operating hours. The volume of oil sample obtained may thus be determined in order to obtain at least 1000 particles, for example. The frequency of sampling may be determined based on the flight hours per year, the maturity of the engine, the typical behavior of the engine type and/or the history of unscheduled engine removal for that engine type, for example. The sample may be obtained and prepared using any suitable method.

At 110, the sample is filtered using any suitable method to obtain particles from the sample. For example, a collected oil sample may be filtered using a very fine filter, such as a 0.22 μm filter, in order to filter out even very small particles (e.g., particles sized as small as 0.5 μm in diameter or smaller). Using such a filter, a sample of about 25 mL may produce a surface sample of about 16 mm in diameter. The particles obtained may range in size from about 0.5 μm to about 1600 μm, for example, although smaller or larger particles may also be obtained. The volume of oil sample filtrated and the size of the sample prepared may vary, such as according to the number of particles in the oil. The volume of oil sample that is filtrated may be determined based on the type of engine and/or the expected normal levels of particles in the oil. In some examples, the obtained density of particles may be 500 particles per $mm^2$, which may be the maximum density that can be used, to reduce or avoid particles overlapping. It may be useful to reduce or avoid particles overlapping, since two or more particles that overlap with each other may be incorrectly detected as one large particle, which may lead to incorrect identification and analysis. In some examples, a sample may have about 5-10% of particles that may not be identifiable, typically due to overlapping, and which may be excluded from the analysis. This exclusion rate may be acceptable.

At 115, each particle is analyzed to determine a plurality of features, such as determination of one or more physical characteristics (e.g., shape and size) and/or chemical composition (e.g., alloy type and chemical composition). SEM may be used for this analysis, although any other suitable methods may be used. The SEM may be coupled to an X-Ray Fluorescence (XRF) detector for carrying out particle analysis. For example, an automated SEM, such as that from Aspex Corporation, may be used. The automated SEM may not require the presence of a human to select the particle that will be analyzed. Software and/or hardware in the system may automatically recognize the presence of a particle and may then automatically move the stage and the electron beam on the particle to perform the particle analysis. The particle size may also be determined automatically. Any other suitable equipment may be used to perform this analysis.

A subset of the particles (e.g., 10% or less) may be analyzed while ensuring a good representation of the whole sample is captured. The analysis of the subset may be normalized to reflect the result for the full sample.

For an average oil sample, about 1500 to 2000 particles may be analyzed. Suitable image analyzer software, such as those conventionally used with SEM, may be used to collect data about particle characteristics and/or composition. Analysis of each particle may produce a respective set of data for that particle, for example there may be up to 70 data points for each particle, the data describing various features of the particle (e.g., size, shape and composition, among others). The total number of data points obtained from analysis of a single sample may be significantly greater than in conventional oil analysis techniques.

The raw data obtained from this analysis may be further processed, in order to account for any measurement error and/or the possible presence of contamination. This further processing may be carried out by categorizing the particles as described below.

At 120, each particle is categorized based on the determined features (e.g., physical characteristics and/or chemical composition). The particles may be categorized in different categories, which may be defined according to one or more of: chemical compositions (e.g., elemental and/or alloy composition), size and morphology. For example, morphology of a particle may be determined by calculating an aspect ratio for the particle (e.g., length to width ratio, for example, where a ratio close to 1 may indicate the particle is close to a spherical shape while a larger value, such as 10, may indicate that the particle is close to a long fiber shape). For example, particles may be classed in a category such as "Environmental", "Metallic", "Non-metallic", "Plating", or "Miscellaneous", among others. Each particle may be further categorized into sub-category levels. As an example, the "Metallic" category may have a level 1 sub-category of "Copper", within which may be level 2 sub-categories of "Bronze" and "Brass". In some examples, five levels of decisions may be used to categorize each particle into a specific level (e.g., metallic, copper, bronze, leaded bronze or machining chip). Categorization of particles may be based on, for example, the absolute chemical composition, the ratio of some elements, the correlation between a specific standard and the particle, the size of the particle and/or the shape of the particle. Categories may be defined according to different alloy compositions, association with one specific manufacturing process and/or association with one particular source (e.g., engine component), for example. Categories may also be defined by the elemental composition or single material of the particles.

Figure 2:
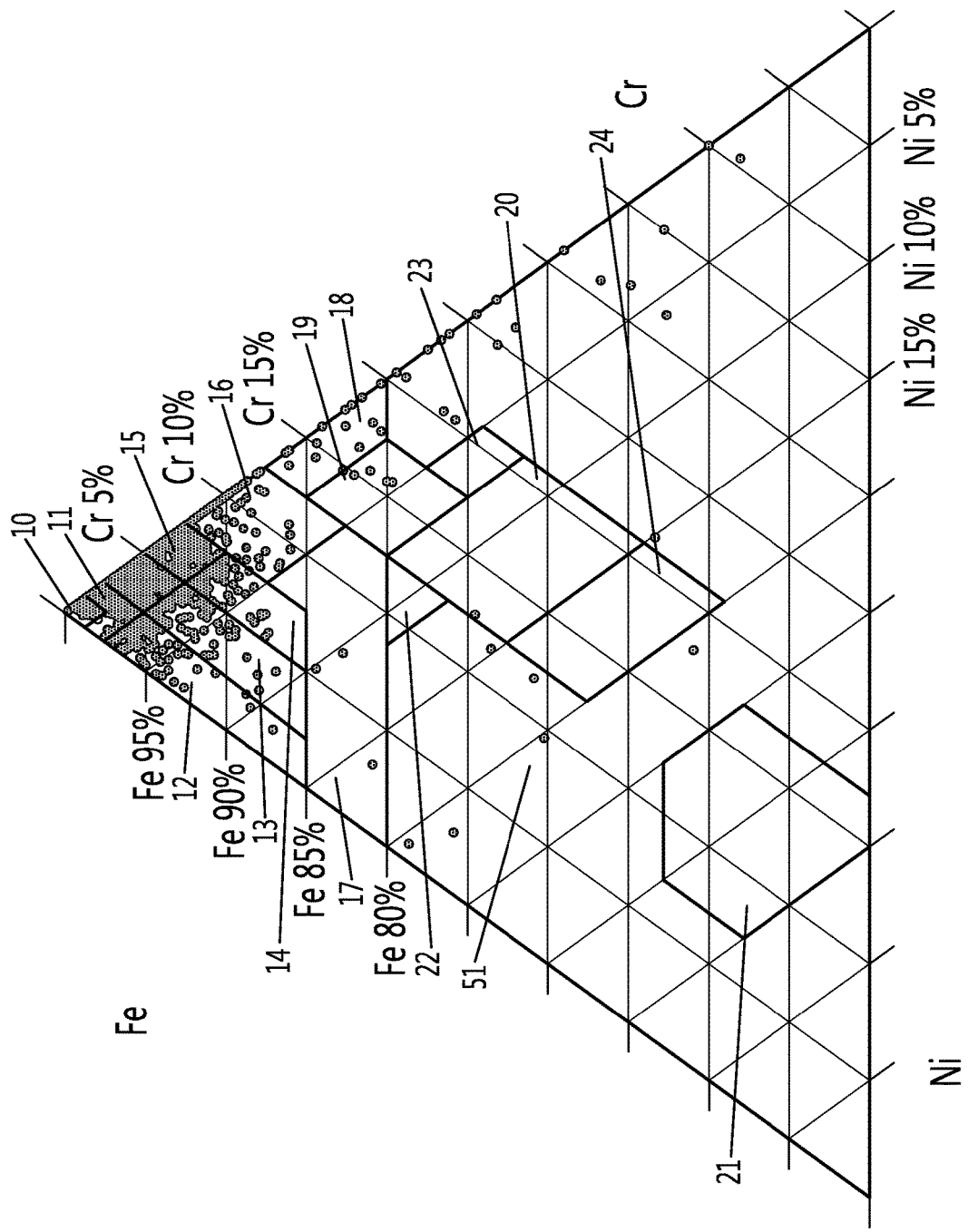
FIG. 2 illustrates an example of different alloy zones that may be used for categorizing particles.

FIG. 2 illustrates an example of how categories may be defined with respect to iron (Fe), chromium (Cr) and nickel (Ni) composition in an alloy. The diagram is divided into different zones, corresponding to different categories. Dots on the diagram illustrate how example particles fall within different zones. The zones may be associated with a particular alloy and/or expected sources of the alloy. For example, zone 15 may be associated with M50, a bearing material. A particle that is categorized as belonging to the category of zone 15 may be expected to originate from a bearing, and its presence may be predictive of bearing wear and/or a failure mechanism related to bearing wear.

Categorization of each particle may be carried out using an algorithm to match each particle to the appropriate category. Each particle may be compared against a historical standard for a category, in order to determine if that particle belongs in that category. Example algorithms for carrying out this categorization include the use of a Cross Probability Match (CPM) Index, as well as logical exclusion tests.

The CPM may be understood as an evaluation of the product of the likelihood of the unknown particle to be the standard (PvS) and the likelihood of the standard to be the unknown particle (SvP). In this example, the likelihood of a match may be based on an evaluation of the elemental composition of the particle compared to that of a historical standard for that category or sub-category.

An example version of CPM uses a linear model, which is based on a linear contribution of each element equal to its concentration. The CPM linear model may be described by the equation:

$$CMP_{ij} = P_j vS_i \times S_i vP_j \times 100$$

where $$P_j vS_i = \sum_k^n \left( \min\left[\frac{E_{P_k}}{E_{S_k}}, \frac{E_{S_k}}{E_{P_k}}\right]^2 \times N_{S_k} \right)$$

-continued $$S_i vP_j = \sum_k^n \left( \min\left[\frac{E_{P_k}}{E_{S_k}}, \frac{E_{S_k}}{E_{P_k}}\right]^2 \times N_{P_k} \right)$$

$$N_{P_k} = \frac{E_{P_k}}{\sum_l^n (E_{P_l})}$$

and $$N_{S_k} = \frac{E_{S_k}}{\sum_l^n (E_{S_l})}$$

and where i denotes the particle being categorized; j denotes the historical standard; n denotes the number of elements of interest used to categorize the particle; $Ep_k$ denotes the concentration of the element k in the particle being categorized; $Es_k$ denotes the concentration of the element k in the historical standard being compared to; $Np_k$ denotes the normalized concentration of the element k in the particle being categorized; $Ns_k$ denotes the normalized concentration of the element k in the historical standard; Tp denotes the summation of the concentration of all elements of interest in the particle; Ts denotes the summation of the concentration of all elements of interest in the historical standard; PvS denotes the probability for the particle to be the historical standard; and SvP denotes the probability for the historical standard to be the particle.

Another example model is CPMQ, the square root version of CPM, which is based on a contribution equal to the squared of its concentration. CPMQ may be used where an element is present in a high percentage (e.g., greater than 5%) in an alloy belonging to the category of interest. The CPM square root model may be described by the equation:

$$CPMQ_{ij} = P_j vS_i^* \times S_i vP_j^* \times 100$$

where $$P_j vS_i^* = \sum_k^n \left( \min\left[\frac{E_{P_k}}{E_{S_k}}, \frac{E_{S_k}}{E_{P_k}}\right]^2 \times N_{S_k}^* \right)$$

$$S_i vP_j^* = \sum_k^n \left( \min\left[\frac{E_{P_k}}{E_{S_k}}, \frac{E_{S_k}}{E_{P_k}}\right]^2 \times N_{P_k}^* \right)$$

$$N_{P_k}^* = \frac{\sqrt{E_{P_k}}}{\sum_l^n (\sqrt{E_{P_l}})}$$

$$N_{S_k}^* = \frac{\sqrt{E_{S_k}}}{\sum_l^n (\sqrt{E_{S_l}})}$$

Using CPM or other suitable statistic techniques to categorize each particle may allow for automation of particle categorization, for example. Use of CPM or other suitable statistical techniques may also allow for categorization of particles while accounting for possible measurement noise and/or contamination, for example.

In some examples, a category (also referred to as a group of interest) may further break down into one or more bins defined according to particle size ranges. For example, particles may be categorized in columns according to size (in μm, in the example shown) and in rows according to composition. In some examples, particles may also be sorted into bins according to particle morphology. In some examples, there may be 84 categories and sub-categories. The categories may be defined based on elemental composition, alloy type, particle origin, or any other suitable category of particle characteristics and composition. Categorizing particles by size and/or shape, as well as composition may allow for distinguishing between one failure mechanism that is characterized by small particles of a given alloy and a different failure mechanism that is characterized by large particles of the same given alloy, for example. Categorizing particles into categories other than simple elemental composition may also allow for discerning particle data patterns that may not be otherwise observed.

For example, a category may represent a generic type of alloy, and may include one or more levels of sub-categories that may further split the category into finer categorization, for example as precisely as the alloy unified number (UNS) of the particles analyzed. For example, a specific alloy may cover two or more categories and/or sub-categories.

Example categories and sub-categories include:

Environmental—sub-categories: calcium, sodium, CalSil (which may originate from cement from an airstrip), dust—earth, talc, vermiculite (which may originate from packaging of the sample) and chlorides (with further sub-category NaCl).

Metallic—sub-categories: iron (which may include further sub-categories of different composition zones such as different steels, and other alloy types), nickel, titanium, copper (with further sub-categories such as brass, bronze and leaded copper), zinc (which may originate from galvanized coating found in the engine filters and is typically found with iron and phosphorus particles also), aluminum, magnesium, cobalt and chromium.

Non-metallic—sub-categories: aluminum/silicon, silicon/aluminum, silicon/magnesium, magnesium/aluminum, fiberglass, asbestos, filter fibers, glass beads and silica.

Others—sub-categories: $MoS_2$, grease with $MoS_2$, lead and contaminated silver.

Plating—sub-categories: tin, silver, cadmium, copper, phosphate-manganese (AMS 2481) and chromium.

Not Categorized

These example categories may be predefined based on knowledge or expectation of what particles would be obtained from an oil sample of a given engine type. The categories may also be defined based on the analysis of the samples. For example, if it appears that most of the particles fall into a few categories, sub-categories may be defined for those few categories in order to more finely categorize the particles. The defined categories may be different for different engine types and/or at different total operating hours, for example.

At 125, the data obtained from categorization of particles is compared with historical data associated with the engine type and/or any data from previous analyses of the same engine. This comparison may be based on a quantification in each category (e.g., a count of particles of certain characteristics, such as certain size and/or morphology, which may be based on the sorting of particles into bins within each category, and may include normalizing the count to a 25 mL sample and for 100% of the area analyzed), to obtain a set of categorized data. The categorized data in each category and/or sub-category, as well as categorized data representative of all categories, may be compared with the historical data.

In an example where an oil sample from an engine is being analyzed, data obtained for the specific oil sample may be compared with other historical data obtained from engines of the same or similar type obtained at equivalent or similar operating hours and/or equivalent or similar operating conditions (e.g., running in a dry or sandy environment vs. a wet environment).

Historical data may be collected as part of the disclosed methods and systems, may be collected using other techniques, may be collected as part of routine maintenance, may be derived from previous records and engine specifications, or may be obtained by any other suitable means. One or more sets of historical data may be represented by an aggregate or general historical model of expected engine wear and/or failure mechanisms for engines of a particular engine type. The historical model may be a simple average of all data for a given engine type at a given operating age, for example. In some examples, a historical model may include an average of all data, expunged of six-sigma results. The model may be adjusted over time as more historical data sets are added to the model. A model based on a larger population of historical data may be a more accurate and precise predictor of engine failure than a model based on a smaller population of historical data. Historical data may include data from different engines of the same engine type at the same or similar operating hours (also referred to as latitudinal data or cross-sectional data), and may also include data from the same engine at different operating hours (also referred to as longitudinal data).

The comparison between the sample data and the historical data may be carried out using any suitable statistical methods. For example, any category with sample data values that fall outside a three sigma range of the historical data may be flagged or highlighted. For example, for a given category the comparison may use the calculation: (sample data−average data)/standard deviation.

In some examples, a composite variation value may be calculated based on the difference between the sample and historical data, for example expressed in standard deviation and/or a weight assigned to each category. For example, a composite index for a low alloy may be calculated as:

$$CI_{LowAlloy} = \sum_{i=10}^{12} \left[ \sum_{j=1}^{5} w_{ij} S_{ij} \right]$$

Where: i is the zone category; j is the particle size category; $S_{ij}$ is the deviation expressed in standard deviation for the particles of the category size j from the zone i; $W_{ij}$ is the weight attributed for the particles of the category size j from the zone l, and the sum of all weight is equal to 1. The weighting factor may be based on historical data and/or the engine model.

At 130, a prediction of any possible future failure and/or failure mechanism is generated. This prediction may be based on the results of the comparison with historical data. For example, a category flagged as being outside a three sigma range of the historical data may be considered to be predictive of failure of an engine part associated with that category. This may be based on trend analysis of analysis results from the same engine or engine type. Corrective action (e.g., engine removal or increased frequency of testing) may be determined based on the engine history and/or expected performance of the engine type, for example. In some examples, prediction of expected failure and/or failure mechanism may involve review by an export, a technical specialist and/or an operator. Examples of predicted mechanism of failure include excess vibration, bearing wear, external contamination following engine maintenance, bearing rubbing, gear degradation, and bearing cage and race degradation, among others A prediction of failure may be based on a combination of two or more factors. For example, comparison results that indicate a given engine has a greater than normal number of small particles in ferrous alloy zone 20 (corresponding to stainless steel) may indicate excessive engine vibration. This result, in addition to comparison data that indicates the engine has an increased number of particles in zone 21 (corresponding to the bearing cage) and submicron particles in zone 15, may together indicate that the engine is exhibiting problems with the bearing, compared to historical data.

A particular engine type may be known to have certain failure patterns, based on historical data. By comparing data for a given engine belonging to that category/sub-category with historical data for that category/sub-category, a prediction may be generated to indicate when the given engine is expected to fail and/or the expected failure mechanism for the given engine. For example, historical data may reveal certain patterns of particle characteristics over time. By comparing the sample particle data of the given engine with the historical pattern over time, a prediction may be generated of where the given engine is in the expected timeline for engine failure.

In some examples, two or more engine types may share the same or similar mechanism of failure. In such cases, historical data of one engine type may be used for failure prediction of the other engine type, historical data of two or more engine types may be compiled together, and/or the sample historical data may be used for failure prediction of two or more engine types, for example.

Using the generated prediction of failure, appropriate action may be taken. For example, where failure of a particular part has been predicted, that part may be replaced and/or monitored with greater frequency. Or, where failure of the engine has been predicted, that engine may be placed on a tighter maintenance and/or oil analysis schedule. For example, the disclosed methods may include performing a maintenance or pre-maintenance action on the engine. Maintenance or pre-maintenance actions that may be performed include, for example, flagging the engine for maintenance (e.g., in a maintenance file), generating a notification to alert a user for the need to perform maintenance, scheduling maintenance for the engine, and performing the appropriate maintenance, among others. The maintenance or pre-maintenance action performed may be dependent on the generated prediction.

The generated prediction may be recorded and saved for further action and/or future reference. The results may also be added to the historical data. An electronic image of the sample may also be stored for future reference and/or further processing.

The present disclosure also provides systems for carrying out the disclosed methods. An example system may include one or more processors (e.g., in a desktop computer, a handheld computer, a workstation, or any other suitable computing device) that executes instructions (e.g., code embodied in a memory coupled to the processor, or in a computer program product such as a CD, DVD or removable memory) in order to carry out the disclosed methods. The system may include one or more apparatuses for carrying out the particle analysis (e.g., apparatus for SEM and/or XRF, including any suitable energy dispersive spectrometer (EDS)). The system may also include one or more memories and/or databases for storing the historical data and/or records of generated predictions of failure.

The present disclosure also provides computer program products and non-transitory computer-readable media, such as a CD, a DVD, and an internal or external memory, embodying computer-executable instructions for carrying out the disclosed methods.

The disclosed methods and systems may allow for monitoring of an engine over time, and may allow for a timeline of expected failure mechanisms to be developed for that engine type.

The disclosed methods and systems may allow for more sensitive and/or earlier detection of possible engine failure, compared to conventional methods. For example, current oil analysis technologies may not identify the composition of each particle, and a relatively high concentration (e.g., more than 10 ppm) of wear metal in the oil sample may be required to detect the presence of abnormal wearing. In some examples, the disclosed methods and systems may allow the detection limit of wear in bearing material to be reduced by a factor of 1000 or more, which may allow for earlier detection of a problem.

In the disclosed methods and systems, the size of the particles may also be taken into account, which may help to avoid potential error caused by the presence of one big particle. For example, a spherical particle of gear material that is 4 µm in diameter will give the same % Fe reading for the total sample as 500 particles of bearing material each 0.5 µm in diameter. If the sizes of the individual particles are not taken into account, this would lead to possible misdiagnosis of bearing wear as being gear wear.

The conventional SOAP technique typically relies on elemental analysis using emission/atomic absorption analysis of particles. The particles analyzed are typically limited to 2-3 µm or smaller. The result of SOAP is typically a quantification of elements (e.g., iron) by volume (e.g., in ppm), without a consideration of particle size, alloy type or shape of the particle, and may produce a relatively small number of data points (e.g., about 30 data points that describe the total quantities of individual elements in the total sample). In the present disclosure, in additional to categories defined by elemental composition, categories may be defined in other ways, such as by alloy type and expected particle origin (e.g., specific engine component that might be the source of the particle), as well as by particle size and shape. These other category definitions may help in identifying data patterns that may not be discernible when categorizing particles only by elemental composition. Further, the presently disclosed methods and systems may consider characteristics of each individual particle, rather than overall characteristics of the total sample.

Conventional oil analysis techniques typically are limited to analysis of relatively large particles (e.g., 30 µm or larger). The presently disclosed methods and systems may allow oil analysis to be carried out on large as well as smaller particles.

Further, conventional techniques typically considered SEM to be unsuitable for routine monitoring of engines. For example SEM typically was considered to be time-consuming and labor-intensive.

In various aspects and embodiments, the present disclosure may provide the ability to identify the composition of wear metal in an oil sample. In some examples, the disclosed methods and systems may provide a low detection limit that may allow the detection of abnormal wearing sufficiently early in the deterioration cycle, giving a chance to fix the problem during a planned maintenance. Early and/or rapid detection of a problem may also give the opportunity to fix the root cause of the problem early, which may help to reduce the total number of problematic engine in the field.

The above description is meant to be exemplary only, and one skilled in the art will recognize that changes may be made to the embodiments described without departing from the scope of the invention disclosed. For example, although the disclosed method has been described in terms of a number of steps, certain steps may be omitted and/or rearranged in order. Although the present disclosure makes reference to oil analysis for predicting failure in an engine, analysis of other fluids (e.g., other lubricants) for failure prediction in other components may be carried out using the disclosed methods and systems. Still other modifications which fall within the scope of the present invention will be apparent to those skilled in the art, in light of a review of this disclosure, and such modifications are intended to fall within the appended claims.

REFERENCES

[1] M. Lukas, D. P. Anderson, Spectro Incorporated, Littleton, Mass. "Rotrode Filter Spectroscopy, Does It have a Place in Commercial or Military Oil Analysis Laboratory".
[2] K. J. Eisentraut, R. W. Newman, C. S. Saba, R. E. Kauffman, and W. E. Rhine, "Spectrometrix oil analysis: detecting engine failures before they occur", Analytical Chemistry 56, August 84, 1086A-1094A.
[3] R. R. Whitlock, Advances in X-Ray Analysis, Volume 40, 1996.

What is claimed is:

1. A method for failure prediction in an engine, the method comprising:
receiving a sample of lubricant fluid from the engine, the sample of lubricant fluid having particles suspended therein;
filtering a plurality of the particles from the sample of lubricant fluid;
collecting raw data representing a plurality of features of each of the plurality of particles filtered from the lubricant fluid of the engine, the engine belonging to an engine type, the plurality of features including at least one physical characteristic and one chemical composition, the collecting of the raw data comprising performing particle analysis using X-ray spectroscopy;
using one or more processors and the raw data:
categorizing each particle into one of a plurality of categories according to at least one of the plurality of features by calculating a likelihood that a given particle belongs to a given category, at least one category being defined by a chemical composition zone within a three-chemical-element system;
quantifying particle physical characteristics in each category to obtain a set of categorized data;
comparing the set of categorized data with at least one set of historical data associated with the engine type, the historical data being retrieved from a database;
evaluating results of the comparing using a set of predefined rules to generate a prediction of any failure or mechanism of failure; and
generating an output indicating the prediction to indicate one or both of the following: when the engine is expected to fail and the mechanism of failure of the engine.

2. The method of claim 1, wherein quantifying comprises determining a number of particles for a given category, and normalizing the number of particles.

3. The method of claim 1, wherein each particle within each category is further sorted into a plurality of bins according to physical characteristics, wherein quantifying the particle physical characteristics in each category comprises determining a number of particles sorted into each bin.

4. The method of claim 1, wherein the physical characteristics comprise at least one of a size and a morphology of each particle.

5. The method of claim 1, wherein the chemical composition comprises an alloy composition of each particle.

6. The method of claim 1, wherein the at least one set of historical data is in the form of a historical model generated from a plurality of sets of historical data.

7. The method of claim 1, wherein the plurality of particles comprises particles smaller than about 30 μm in diameter.

8. The method of claim 1, wherein the plurality of particles comprises particles sized in the range of about 0.5 μm to about 1600 μm in diameter.

9. The method of claim 1, wherein the plurality of categories comprises at least one sub-category.

10. The method of claim 1, wherein the plurality of categories comprises at least one category defined according to: elemental composition, alloy composition and particle source.

11. The method of claim 1, wherein the comparison comprises at least one of a calculation of deviation of the categorized data from the historical data, and a calculation of variation of the categorized data from the historical data.

12. The method of claim 1, wherein the comparison comprises at least one of a comparison of the categorized data in each category to the historical data, and a comparison of a composite of the categorized data to the historical data.

13. The method of claim 1, wherein the predicted mechanism of failure comprises at least one of a determination of premature wear of an engine component and a determination of an expected failure of an engine.

14. The method of claim 13 wherein the predicted mechanism of failure includes at least one of: excess vibration, bearing wear, external contamination following engine maintenance, bearing rubbing, gear degradation, and bearing cage and race degradation.

15. The method of claim 1, wherein the engine is an aircraft engine.

16. The method of claim 1, wherein using X-ray spectroscopy includes using X-ray fluorescence.

17. A system for fluid analysis, the system comprising one or more processors and a memory containing machine-readable instructions for execution by the one or more processors of the system, the machine-readable instructions causing the one or more processors of the system to carry out the steps performed by the one or more processors in the method of claim 1.

18. The system of claim 17 further comprising spectroscopy equipment for carrying out particle analysis.

19. A non-transitory computer-readable medium or media embodying computer-executable instructions configured for causing the one or more processors of the method of claim 1 to carry out the steps performed by the one or more processors in the method of claim 1.

* * * * *